(12) United States Patent
Ueda (10) Patent No.: US 11,027,110 B2
(45) Date of Patent: Jun. 8, 2021

(54) MEDICAL CONNECTOR

(71) Applicant: TERUMO KABUSHIKI KAISHA, Tokyo (JP)

(72) Inventor: Yasuhiro Ueda, Kofu (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 92 days.

(21) Appl. No.: 15/934,699

(22) Filed: Mar. 23, 2018

(65) Prior Publication Data

US 2018/0207418 A1    Jul. 26, 2018

Related U.S. Application Data

(63) Continuation of application No. PCT/JP2016/004313, filed on Sep. 21, 2016.

(30) Foreign Application Priority Data

Sep. 24, 2015    (JP) .............................. JP2015-187120

(51) Int. Cl.
*A61M 39/10* (2006.01)
*A61M 39/26* (2006.01)
(Continued)

(52) U.S. Cl.
CPC ...... *A61M 39/1011* (2013.01); *A61M 39/045* (2013.01); *A61M 39/26* (2013.01);
(Continued)

(58) Field of Classification Search
CPC .. A61M 39/10; A61M 39/1011; A61M 39/26; A61M 39/225; A61M 39/045;
(Continued)

(56) References Cited

U.S. PATENT DOCUMENTS 4,254,773 A * 3/1981 Waldbillig ........ A61M 39/1055
285/281
5,071,413 A * 12/1991 Utterberg .............. A61M 5/162
604/533
(Continued)

FOREIGN PATENT DOCUMENTS

| JP | 2003-339878 A | 12/2003 |
| JP | 4075972 B2 | 4/2008 |
| WO | WO-2014/049819 A1 | 4/2014 |

OTHER PUBLICATIONS

International Search Report with English translation and Written Opinion issued in International Application No. PCT/JP2016/004313 dated Dec. 27, 2016.

*Primary Examiner* — Nathan R Price
*Assistant Examiner* — Courtney B Fredrickson
(74) *Attorney, Agent, or Firm* — Foley & Lardner LLP (57) ABSTRACT

A medical connector includes: a male connector portion that is connectable to a closed female connector portion of another medical connector, the closed female connector portion comprising an opening formed on a top wall, and a valve body blocking the opening and having a slit, an outer peripheral edge portion of the valve body being secured to the top wall; wherein the male connector portion includes: a tubular body having an outer diameter equal to or less than a length that is twice a distance between a center of a top surface of the valve body and an end of the slit that is radially furthest from the center, the tubular body being insertable into the slit, a limiting portion configured to limit an insertion depth of the tubular body, a sealing portion configured to surround the slit, and a locking portion.

8 Claims, 4 Drawing Sheets

(51) Int. Cl.
*A61M 39/04* (2006.01)
*A61M 39/22* (2006.01)
*F16L 37/38* (2006.01)

(52) U.S. Cl.
CPC ............... *A61M 2039/1038* (2013.01); *A61M 2039/229* (2013.01); *F16L 37/38* (2013.01)

(58) Field of Classification Search
CPC .. A61M 2039/1016; A61M 2039/1038; A61M 2039/229; A61M 2039/1072
See application file for complete search history.

(56) References Cited

U.S. PATENT DOCUMENTS

| | | | | |
|---|---|---|---|---|
| 5,492,147 | A * | 2/1996 | Challender | F16L 29/005 |
| | | | | 137/614.05 |
| 7,241,285 | B1 * | 7/2007 | Dikeman | A61M 39/045 |
| | | | | 604/533 |
| 9,044,585 | B2 * | 6/2015 | Masuda | A61M 39/045 |
| 2005/0090805 | A1 * | 4/2005 | Shaw | A61M 39/26 |
| | | | | 604/523 |
| 2008/0306469 | A1 * | 12/2008 | Masuda | A61M 39/045 |
| | | | | 604/535 |
| 2013/0079744 | A1 * | 3/2013 | Okiyama | A61J 1/2089 |
| | | | | 604/408 |

* cited by examiner

MEDICAL CONNECTOR

CROSS-REFERENCE TO RELATED APPLICATIONS

The present application is a bypass continuation of PCT Application No. PCT/JP2016/004313, filed on Sep. 21, 2016, which claims priority to Japanese Application No. 2015-187120, filed on Sep. 24, 2015. The contents of these applications are hereby incorporated by reference in their entireties.

BACKGROUND

The present disclosure relates to a medical connector having a male connector portion, in particular, to a medical connector having a male connector portion.

Conventionally, medical connectors that are used, for example, in various medical equipment, infusion fluid containers, or fluid conveying devices for connecting tubular bodies of medical devices have been known. There are various known types of such connectors, one of which includes a closed female connector portion having an opening formed on a top wall, and a valve body that blocks the opening and has a slit, with an outer peripheral edge portion of the valve body being secured to a bottom surface of the top wall.

In general, when connecting a male luer that has an external diameter and a taper angle that conform to ISO 594-1 to a closed female connector portion configured as described above, the male luer is inserted into the opening while pushing the valve into the opening so that when being disconnected, there is a backflow corresponding to the volume of the male luer and the valve body that have been filling the opening. Such a backflow can have negative effects in particular conditions of use. It is thus preferred that the amount of backflow during disconnection is as small as possible.

Medical connectors that suppress such backflow are known, for example, from JP 4075972 B1 and JP 2003-339878 A, each of which discloses a medical connector that includes a dedicated male connector portion that does not conform to ISO 594-1 and that is capable of being connected to a closed female connector portion configured as described above.

SUMMARY

In JP 4075972 B, the male connector portion of the medical connector includes a tubular body that can be inserted into a slit of a valve body, and achieves a seal only by intimate contact between an outer peripheral surface of the tubular body and the slit of the valve body. Thus, in the medical connector disclosed in JP 4075972 B, increasing sealing characteristics requires the resilience of the valve body to be set high, which in turn may have ill effects on the insertability of the tubular body.

In JP 2003-339878 A, the male connector portion of the medical connector includes a tubular body that can be inserted into a slit of a valve body, and the tubular body is inversely tapered so that the tubular body is locked to the valve body by the resilience of the valve body after being inserted. Thus, in the medical connector disclosed in JP 2003-339878 A, inadvertent disengagement may occur when a relatively large external force is applied to the male connector portion.

Embodiments described herein have been developed to address such problems. One object of certain embodiments is to provide a medical connector having a male connector portion, wherein the medical connector reduces the amount of backflow when being disconnected from a closed female connector portion of another medical connector, advantageously improves sealing characteristics, and inhibits inadvertent disengagement of the male connector portion.

According to one embodiment, a medical connector includes a male connector portion that is connectable to a closed female connector portion of another medical connector, wherein the closed female connector portion has an opening formed on a top wall, and a valve body blocking the opening and having a linear slit, an outer peripheral edge portion of the valve body being secured to a bottom surface of the top wall. The male connector portion includes a tubular body having an outer diameter equal to or less than a length that is twice the distance between the center of a top surface of the valve body and an end of the slit radially spaced furthest from the center, the tubular body being insertable into the slit, a limiting portion that limits an insertion depth of the tubular body into the opening by abutting against the other medical connector when the male connector portion is connected to the closed female connector portion, a sealing portion that surrounds the slit and directly contacts the top surface of the valve body or a top surface of the top wall when the male connector portion is connected to the closed female connector portion, and a locking portion that keeps the male connector portion connected to the closed female connector portion.

In one aspect, the limiting portion limits the insertion depth of the tubular body into the opening by abutting against the top surface of the top wall when the male connector portion is connected to the closed female connector portion.

In one aspect, the male connector portion includes an enlarged portion connected to a base end side of the tubular body and having a widened outer diameter, and that the enlarged portion is the sealing portion that surrounds the slit and directly contacts the top surface of the valve body when the male connector portion is connected to the closed female connector portion.

In one aspect, the limiting portion includes an O-ring as the sealing portion that surrounds the slit and directly contacts the top surface of the top wall when the male connector portion is connected to the closed female connector portion.

In one aspect, an external thread is provided on an outer peripheral surface of the closed female connector portion, and that the locking portion is an internal thread engageable with the external thread.

In one aspect, that the closed female connector portion is connectable to a male luer having an outer diameter and a taper angle that conform to ISO 594-1.

Certain embodiments described herein are capable of reducing the volume of the tubular body and the valve body that are pushed into the opening in the top wall of the closed female connector portion when the male connector portion is connected to the closed female connector portion and thereby reducing the amount of backflow when the male connector portion is disconnected from the closed female connector portion. In addition, when the male connector portion is connected to the closed female connector portion, the sealing portion surrounds the slit and directly contacts the top surface of the valve body or the top surface of the top wall to thereby advantageously improve sealing characteristics. Furthermore, the connection can be maintained by the locking portion.

Thus, according to certain embodiments, the medical connector having the male connector portion is capable of reducing the amount of backflow when being disconnected from the closed female connector portion on the other medical connector, advantageously improving the sealing characteristics, and inhibiting inadvertent disengagement of the male connector portion.

DESCRIPTION OF EMBODIMENTS

A medical connector 1 according to embodiments will be described below in detail, by way of example, with reference to FIGS. 1 to 4.

It should be noted that, herein, an up-down direction of the medical connector 1 refers to a direction along a central axis O of a male connector portion 2 of the medical connector 1, an upper part refers to a base end side (upper part of FIG. 2) of a tubular body 2a of the male connector portion 2, and a lower part refers to a distal end side (lower part of FIG. 2) of the tubular body 2a. An up-down direction of a medical connector 10, which is an example of another medical connector that can be used together with the medical connector 1, refers to a direction along a central axis O of a closed female connector portion 11 of the medical connector 10, an upper part refers to a side (upper part of FIG. 2) on which a top wall 11b of the closed female connector portion 11 is positioned, and a lower part refers to a side (lower part of FIG. 2) on which a bottom flange 11d of the closed female connector portion 11 is positioned.

Figure 1:
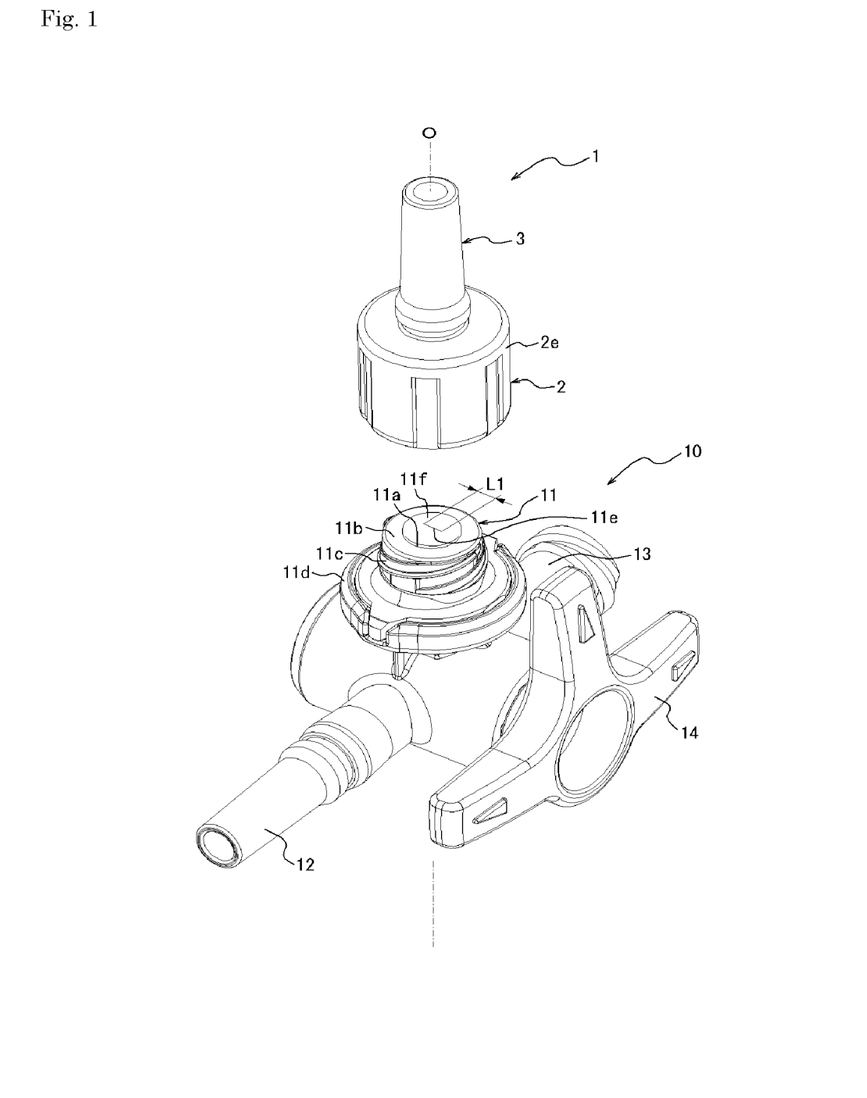
FIG. 1 is a perspective view showing a medical connector according to one embodiment and an example of another medical connector that can be used together with the medical connector, prior to connection of the two medical connectors.
Figure 2:
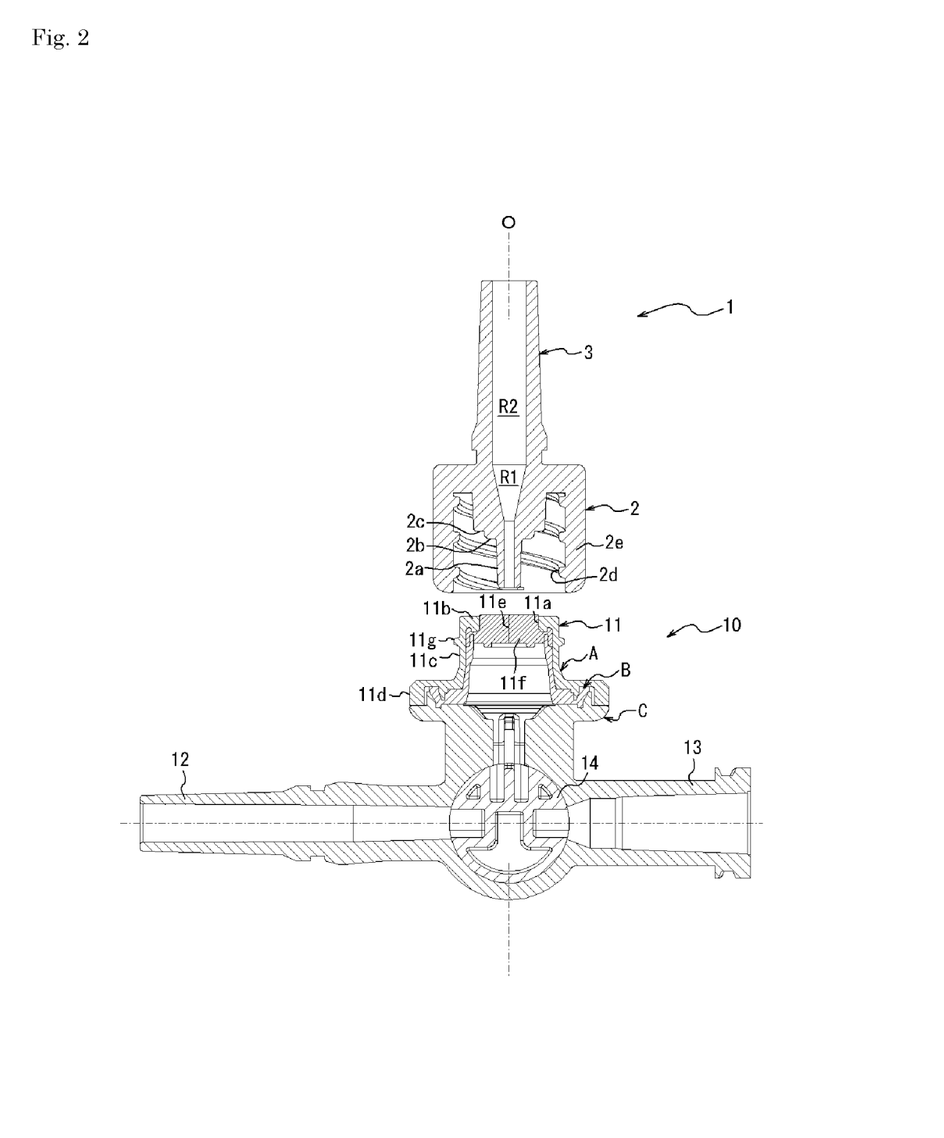
FIG. 2 is a longitudinal cross-sectional view of the two medical connectors shown in FIG. 1 prior to connection.

As shown in FIGS. 1 and 2, the medical connector 1 according to this embodiment includes the male connector portion 2 at one end and a medical device connecting portion 3 at the other end. The medical device connecting portion 3 in this embodiment has a cylindrical shape to which a tubular body of a medical device such as a medical tube can be connected to an outer peripheral surface thereof. The medical device connecting portion 3 may be configured, for example, as a female connector portion, in which case the female connector portion preferably has an internal diameter and a taper angle that conform to ISO 594-1.

The male connector portion 2 has the tubular body 2a, an enlarged portion 2b, a limiting portion 2c, and a locking portion 2d. The tubular body 2a has a cylindrical shape that extends along the central axis O of the male connector portion 2. The enlarged portion 2b has a cylindrical shape with a widened outer diameter connected to the base end side of the tubular body 2a. The limiting portion 2c has a cylindrical shape with a widened outer diameter connected to the base end side of the enlarged portion 2b. In this embodiment, the locking portion 2d is an internal thread provided on an inner peripheral surface of a locking barrel 2e that has a closed-top cylindrical shape connected to the base end side of the limiting portion 2c. In this embodiment, the locking portion 2d is an internal thread that conforms to ISO 594-2.

The locking barrel 2e is integrally formed on the base end side portion of the limiting portion 2c, but alternatively, the locking barrel 2e may be rotatably and unreleasably fittingly retained by the base end side portion of the limiting portion 2c. A flow path R1 is provided along the central axis O inside the male connector portion 2 and is in communication with a flow path R2 that is provided inside the medical device connecting portion 3. The tubular body 2a in this embodiment has a length that does not protrude from a distal end of the locking barrel 2e. Such a length reduces the possibility of contact of the tubular body 2a with the outside and suppresses contamination by such contact.

FIGS. 1 and 2 also show the medical connector 10, which is an example of another medical connector that can be used together with the medical connector 1 according to this embodiment. The medical connector 10 includes the closed female connector portion 11 to which the male connector portion 2 of the medical connector 1 can be connected. In this embodiment, the medical connector 10 is a three-way stopcock that includes two medical device connecting portions (a male luer 12 and a female luer 13), the closed female connector portion 11, which is a co-infusion portion, and a flow path switching member 14. However, the medical connector 10 is not limited to such a three-way stopcock, and may be, for example, a T-connector without the flow path switching member 14, a Y-connector, or a co-infusion plug that includes one medical device connecting portion (male luer) and the closed female connector portion 11.

Figure 3:
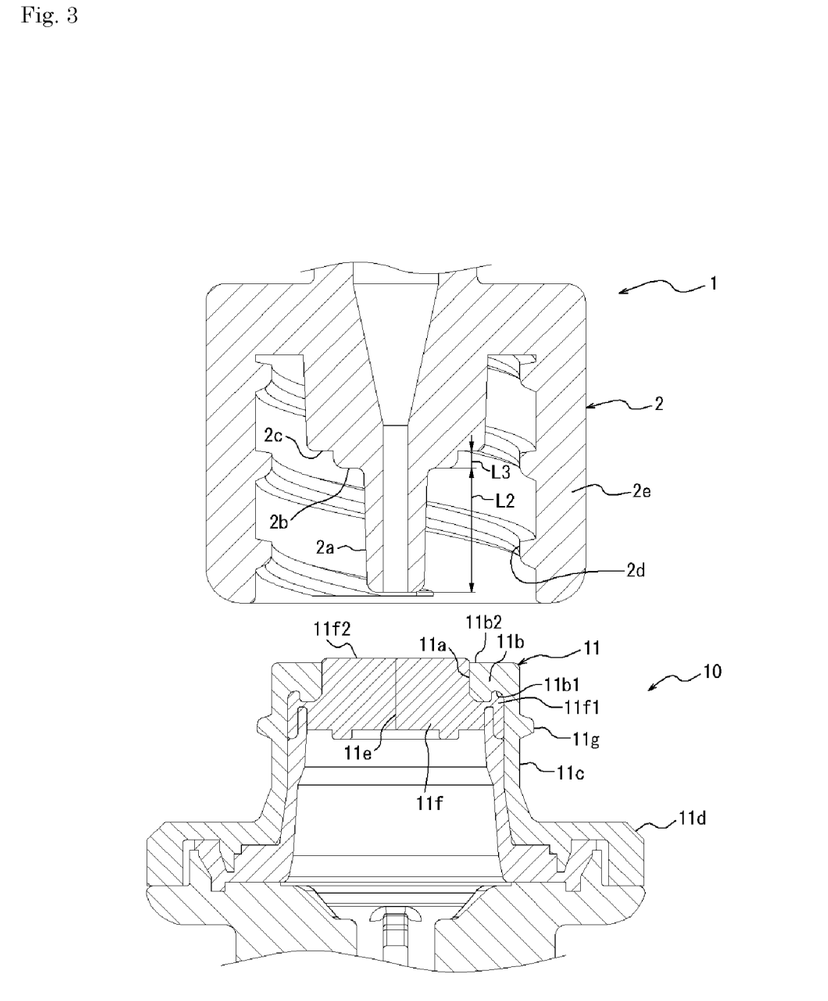
FIG. 3 is an enlarged view of a portion of FIG. 2.

The closed female connector portion 11 includes the annular top wall 11b having a circular opening 11a in the center, a cylindrical peripheral wall 11c depending from an outer peripheral edge of the top wall 11b, and the annular bottom flange 11d extending outwardly from a lower end of the peripheral wall 11c. The closed female connector portion 11 also includes a valve body 11f of an elastic material that blocks the opening 11a and has a slit 11e. The slit 11e in this embodiment is linear and is positioned in the center of a top surface 11f2 of the valve body 11d. The slit 11e is not limited to such a straight line shape and, for example, may be cross-shaped or Y-shaped extending radially from the center of the top surface 11f2 of the valve body 11f. In the case in which the slit 11e is cross-shaped, the slit 11e is preferably configured as four linear portions of equal lengths extending at intervals of 90° in the circumferential direction from the center of the top surface 11f2. In the case in which the slit 11e is Y-shaped, the slit 11e is preferably configured as three linear portions of equal lengths extending at intervals of 120° in the circumferential direction from the center of the top surface 11f2. As shown in FIG. 3 in which a portion of FIG. 2 is enlarged, an outer peripheral edge portion 11f1 of the valve body 11f is secured by abutting a bottom surface 11b1 of the top wall 11b. On an outer peripheral surface of the peripheral wall 11c is formed an external thread 11g that corresponds to the internal thread as the locking portion 2d.

As shown in FIG. 2, the medical connector 10 of this example includes a cap A, a holder B, a housing C, and the flow path switching member 14. The cap A forms the top wall 11b, an outer peripheral portion of the peripheral wall 11c, and an upper portion of the bottom flange 11d. The holder B forms an inner peripheral portion of the peripheral wall 11c and a middle portion of the bottom flange 11d. The cap A and the holder B sandwich the outer peripheral edge portion 11*f*1 of the valve body 11*f*. The housing C forms a lower portion of the bottom flange 11*d* and the two medical device connecting portions (male luer 12 and female luer 13). However, the medical connector 10 is not limited to such a configuration, and various modifications are possible. For example, the holder B and the housing C may be integrally formed.

The closed female connector portion 11 of the medical connector 10 of this example is configured such that a male luer (not shown) having an outer diameter and a taper angle that conform to ISO 594-1 can be connected thereto. Specifically, by inserting such a male luer into the opening 11*a* while pushing the valve body 11*f* into the opening 11*a*, the male luer can be connected to the closed female connector portion 11. The closed female connector portion 11 of this example can maintain a connection with a male lock luer having a locking portion as mentioned above by engaging the locking portion with the external thread 11*g*. In addition, the closed female connector portion 11 of this example can maintain a connection with a male slip luer without a locking portion as mentioned above by fitting an outer peripheral surface of the male luer to an inner peripheral surface of the top wall 11*b*.

Thus, because the closed female connector portion 11 of the medical connector 10 of this example is configured such that a male luer having an outer diameter and a taper angle that conform to ISO 594-1 can be connected thereto, versatility is ensured. Under conditions of use where occurrences of backflow are not a concern, using such a male luer can also ensure a relatively large flow rate. On the other hand, for conditions of use such as, in particular, administering medication to a premature baby, it is preferable to keep the amount of backflow as low as possible. Under such a condition of use, it would be advantageous to use the medical connector 1 according to this embodiment.

Figure 4:
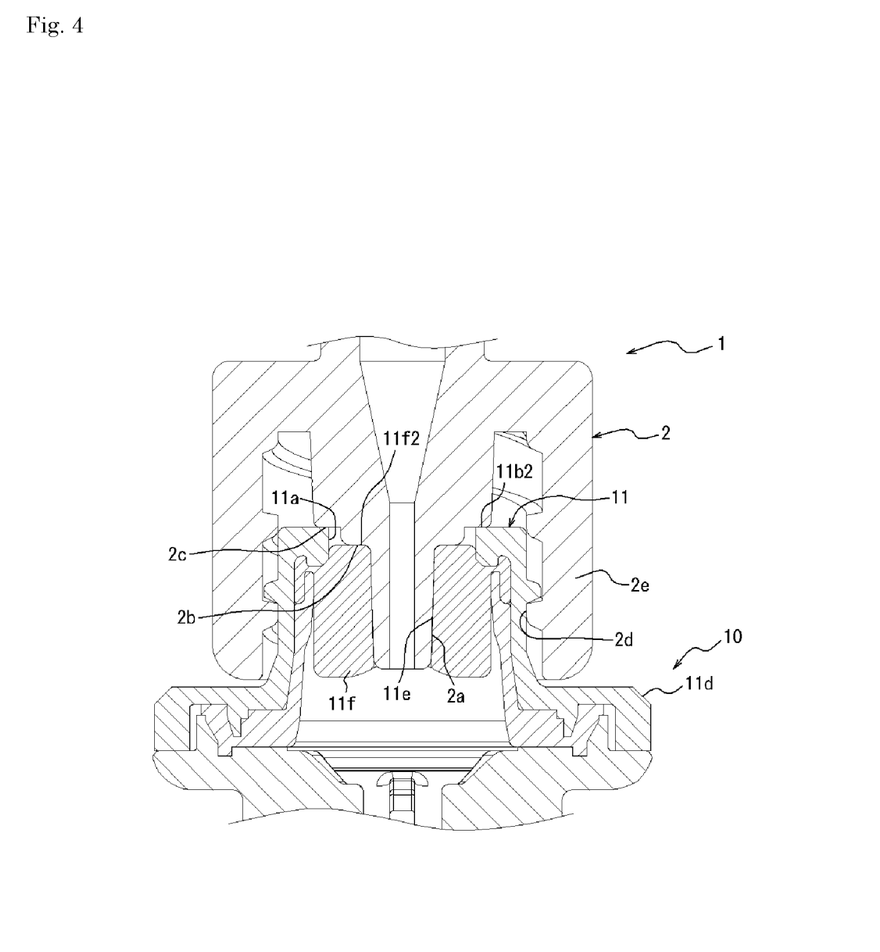
FIG. 4 is a longitudinal cross-sectional view of the two medical connectors shown in FIG. 1 after connection pursuant to FIG. 3.

FIG. 3 shows the male connector portion 2 of the medical connector 1 and the closed female connector portion 11 of the medical connector 10 prior to connection, and FIG. 4 shows them after connection. The tubular body 2*a* of the male connector portion 2 has an outer diameter equal to or less than a length L1 (see FIG. 1) that is twice the distance between the center of the top surface 11*f*2 of the valve body 11*f* and an end of the slit 11*e* that is radially spaced furthest from the center, and is insertable into the slit 11*e*. In other words, the tubular body 2*a* of the male connector portion 2 has an outer diameter equal to or less than the length L1 of the straight line-shaped slit 11*e* of the valve body 11*f*, and is insertable into the slit 11*e*. The "length L1 that is twice the distance between the center of the top surface 11*f*2 of the valve body 11*f* and an end of the slit 11*e* that is radially spaced furthest from the center" is in this example shorter than a distal end outer diameter of the male luer having an outer diameter and a taper angle that conform to ISO 594-1. A length L2 (see FIG. 3) of the tubular body 2*a* is equal to or greater than half the thickness (thickness at the position at which the slit 11*e* is formed) of the valve body 11*f*, and is equal to or shorter than a length such that the tubular body 2*a* abuts against the housing C. Specifically, in this example, the length L2 of the tubular body 2*a* is preferably 2.0 to 7.5 mm.

The enlarged portion 2*b* of the male connector portion 2 functions as a sealing portion that surrounds the slit 11*e* and directly contacts the top surface 11*f*2 of the valve body 11*f* when the male connector portion 2 is connected to the closed female connector portion 11. The outer diameter of the enlarged portion 2*b* is smaller than a diameter of the opening 11*a* in the top wall 11*b* and is greater than the "length L1 that is twice the distance between the center of the top surface 11*f*2 of the valve body 11*f* and an end of the slit 11*e* that is radially spaced furthest from the center." A length L3 of the enlarged portion 2*b* is preferably 2.0 mm or less. This is because if it is greater than 2.0 mm, the amount of backflow cannot be sufficiently reduced. Although the enlarged portion 2*b* in this embodiment has a cylindrical shape with a widened outer diameter connected to the base end side of the tubular body 2*a*, it is not limited thereto. For example, the enlarged portion 2*b* may have a polygonal shape that surrounds the slit 11*e* and directly contacts the top surface 11*f*2 of the valve body 11*f*.

The limiting portion 2*c* of the male connector portion 2 is configured to limit an insertion depth of the tubular body 2*a* into the opening 11*a* by abutting against the medical connector 10 (a top surface 11*b*2 of the top wall 11*b* in this embodiment) when the male connector portion 2 is connected to the closed female connector portion 11. The outer diameter of the limiting portion 2*c* is greater than the diameter of the opening 11*a*. The diameter of the opening 11*a* in this example is greater than the distal end outer diameter of the male luer having an outer diameter and a taper angle that conform to ISO 594-1. Although the limiting portion 2*c* in this embodiment is a cylindrical portion having an outer diameter greater than the opening 11*a*, it is not limited thereto. The limiting portion 2*c* may include an O-ring as the sealing portion that surrounds the slit 11*e* and directly contacts the top surface 11*b*2 of the top wall 11*b* when the male connector portion 2 is connected to the closed female connector portion 11. In such a configuration, the enlarged portion 2*b* may not always be required. The limiting portion 2*c* may also be a plurality of radially extending ribs that are arranged circumferentially spaced apart.

Furthermore, in this embodiment, the limiting portion 2*c* is provided at a portion that abuts against the top surface 11*b*2 of the top wall 11*b*, though alternatively, for example, a portion that abuts against the bottom flange 11*d* may be provided on the distal end of the locking barrel 2*e* such that this portion functions as the limiting portion. That is, in this case, the distal end of the locking barrel 2*e* abuts against the bottom flange 11*d* of the medical connector 10 as the limiting portion to limit the insertion depth of the tubular body 2*a* into the opening 11*a*.

As described above, the medical connector 1 according to this embodiment includes the male connector portion 2 that can be connected to the closed female connector portion 11 of the other medical connector 10, wherein the closed female connector portion 11 includes the opening 11*a* formed on the top wall 11*b*, and the valve body 11*f* that blocks the opening 11*a* and has the linear slit 11*e*, the outer peripheral edge portion 11*f*1 of the valve body 11*f* being secured to the bottom surface 11*b*1 of the top wall 11*b*. The male connector portion 2 includes the tubular body 2*a* that has an outer diameter equal to or less than the length L1 that is twice the distance between the center of the top surface 11*f*2 of the valve body 11*f* and an end of the slit 11*e* that is radially spaced furthest from the center, the tubular body 2*a* being insertable into the slit 11*e*, the limiting portion 2*c* that limits the insertion depth of the tubular body 2*a* into the opening 11*a* by abutting against the other medical connector 10 when the male connector portion 2 is connected to the closed female connector portion 11, the sealing portion (enlarged portion 2*b*) that surrounds the slit 11*e* and directly contacts the top surface 11*f*2 of the valve body 11*f* when the male connector portion 2 is connected to the closed female connector portion 11, and the locking portion 2d that keeps the male connector portion 2 connected to the closed female connector portion 11.

Thus, this embodiment is capable of reducing the volume of the tubular body 2a and the valve body 11f that are pushed into the opening 11a in the top wall 11b of the closed female connector portion 11 when the male connector portion 2 is connected to the closed female connector portion 11 and thereby reducing the amount of backflow when the male connector portion 2 is disconnected from the closed female connector portion 11. In addition, when the male connector portion 2 is connected to the closed female connector portion 11, the sealing portion (enlarged portion 2b) surrounds the slit 11e and directly contacts the top surface 11f2 of the valve body 11f to thereby advantageously improve sealing characteristics. Furthermore, the connection can be maintained by the locking portion 2d.

In the medical connector 1 according to this embodiment, the limiting portion 2c limits the insertion depth of the tubular body 2a into the opening 11a by abutting against the top surface 11b2 of the top wall 11b when the male connector portion 2 is connected to the closed female connector portion 11. Thus, this embodiment is capable of accurately limiting the insertion depth of the tubular body 2a.

In the medical connector 1 according to this embodiment, the male connector portion 2 includes the enlarged portion 2b that is connected to the base end side of the tubular body 2a and has a widened outer diameter, the enlarged portion 2b being the sealing portion that surrounds the slit 11e and directly contacts the top surface 11f2 of the valve body 11f when the male connector portion 2 is connected to the closed female connector portion 11. Thus, this embodiment enhances the sealing characteristics by a simple configuration.

In the case in which the medical connector 1 according to this embodiment is configured such that the limiting portion 2c includes the O-ring as the sealing portion that surrounds the slit 11e and directly contacts the top surface 11b2 of the top wall 11b when the male connector portion 2 is connected to the closed female connector portion 11, good sealing characteristics can be exhibited even when plastic deformation occurs to the valve body 11f due to repeated connection and disconnection.

The medical connector 1 according to this embodiment has the external thread 11g provided on the outer peripheral surface of the closed female connector portion 11, with the locking portion 2d being an internal thread that is engageable with the external thread 11g. Thus, the connection between the connectors can be reliably maintained by a simple configuration.

Furthermore, the medical connector 1 according to this embodiment is configured such that a male luer having an outer diameter and a taper angle that conform to ISO 594-1 can be connected to the closed female connector portion 11. Thus, this embodiment is capable of achieving the male connector portion 2 that conforms to the ISO compliant versatile closed female connector portion 11 and that reduces the amount of backflow.

While certain embodiments are described above, other variations are possible within the scope of the claims. For example, although the locking portion 2d and the closed female connector portion 11 maintain a connection via a thread, it need not necessarily be limited to a thread, and the connection may be maintained, for example, through the engagement of a groove with a projection.

REFERENCE NUMERAL LIST

1 Medical connector
2 Male connector portion
2a Tubular body
2b Enlarged portion
2c Limiting portion
2d Locking portion
2e Locking barrel
3 Medical device connecting portion
10 Another medical connector
11 Closed female connector portion
11a Opening
11b Top wall
11b1 Bottom surface
11b2 Top surface
11c Peripheral wall
11d Bottom flange
11e Slit
11f Valve body
11f1 Outer peripheral edge portion
11f2 Top surface
11g External thread
12 Male luer
13 Female luer
14 Flow path switching member
O Axis
R1, R2 Flow path
A Cap
B Holder
C Housing
L1 to L3 Length

What is claimed is:

1. An assembly comprising:
    a closed female connector portion that comprises an opening formed in a top wall, and a valve body blocking the opening and having a slit, an outer peripheral edge portion of the valve body being secured to the top wall; and
    a male connector portion that is connectable to the closed female connector portion of a medical connector,
    wherein the male connector portion comprises:
        a limiting portion configured to limit an insertion depth of a tubular body into the opening by directly contacting a top surface of the top wall of the closed female connector portion of the medical connector when the male connector portion is connected to the closed female connector portion,
        an enlarged portion extending from a distal end side of the limiting portion and configured to surround the slit and to directly contact a top surface of the valve body when the male connector portion is connected to the closed female connector portion, wherein a diameter of the enlarged portion at a distal end side of the enlarged portion is less than a diameter of the limiting portion,
        the tubular body extending from the distal end side of the enlarged portion and being insertable into the slit, wherein an outer diameter of the tubular body is less than an outer diameter of the enlarged portion, and wherein the outer diameter of the tubular body is equal to or less than a length that is twice a distance between a center of the top surface of the valve body and an end of the slit that is radially furthest from the center, and
        a locking portion configured to keep the male connector portion connected to the closed female connector portion.

2. The assembly according to claim 1, wherein:
the locking portion is an internal thread that is engageable with an external thread that is located on an outer peripheral surface of the closed female connector portion.

3. The assembly according to claim 1, wherein the closed female connector portion is connectable to a male luer having an outer diameter and a taper angle conforming to ISO 594-1.

4. The assembly according to claim 1, wherein a proximal most end of the tubular body is located at a distal most end of the enlarged portion.

5. The assembly according to claim 1, wherein the limiting portion, the enlarged portion, and the tubular body are immovably fixed with respect to one another.

6. The assembly according to claim 1, wherein the tubular body is immovably fixed with respect to the limiting portion.

7. The assembly according to claim 1, wherein the limiting portion, the enlarged portion, and the tubular body are formed as a single piece.

8. The assembly according to claim 1, wherein the diameter of the limiting portion is greater than a diameter of the opening of the closed female connector portion.

* * * * *